(12) United States Patent
McFarlin et al.

(10) Patent No.: US 8,241,313 B2
(45) Date of Patent: Aug. 14, 2012

(54) INSTRUMENT AND SYSTEM FOR SURGICAL CUTTING AND EVOKED POTENTIAL MONITORING

(75) Inventors: Kevin McFarlin, Jacksonville, FL (US); David Reinker, Ponte Vedra Beach, FL (US); William C. Brunnett, Jacksonville, FL (US); Michael Ferrell, Orange Park, FL (US)

(73) Assignee: Medtronic Xomed, Inc., Jacksonville, FL (US)

( * ) Notice: Subject to any disclaimer, the term of this patent is extended or adjusted under 35 U.S.C. 154(b) by 301 days.

(21) Appl. No.: 12/761,548

(22) Filed: Apr. 16, 2010

(65) Prior Publication Data

US 2010/0198219 A1 Aug. 5, 2010

Related U.S. Application Data

(63) Continuation of application No. 11/260,503, filed on Oct. 27, 2005, now Pat. No. 7,717,932.

(51) Int. Cl.
*A61B 17/32* (2006.01)

(52) U.S. Cl. ..................................... 606/170

(58) Field of Classification Search .................. 606/37, 606/39, 45, 79, 167, 170, 172, 174
See application file for complete search history.

(56) References Cited

U.S. PATENT DOCUMENTS

| | | | |
|---|---|---|---|
| 3,835,858 A | 9/1974 | Hagen | |
| 3,847,154 A | 11/1974 | Nordin | |
| 4,962,766 A | 10/1990 | Herzon | |
| 5,196,015 A | 3/1993 | Neubardt | |
| 5,257,990 A | 11/1993 | Nash | |
| 5,284,153 A | 2/1994 | Raymond et al. | |
| 5,284,154 A | 2/1994 | Raymond et al. | |
| 5,383,876 A | 1/1995 | Nardella | |
| 5,474,558 A | 12/1995 | Neubardt | |
| 5,584,843 A | 12/1996 | Wulfman et al. | |
| 5,913,867 A | 6/1999 | Dion | |
| 5,928,158 A | 7/1999 | Aristides | |
| 6,139,545 A | 10/2000 | Utley et al. | |
| 6,298,256 B1 | 10/2001 | Meyer | |
| 6,312,392 B1 | 11/2001 | Herzon | |
| 6,423,070 B1 | 7/2002 | Zeppelin | |
| 6,466,817 B1 | 10/2002 | Kaula et al. | |

(Continued)

FOREIGN PATENT DOCUMENTS

WO 2005/074831 A2 8/2005

(Continued)

OTHER PUBLICATIONS

Silverstein Institute article entitled "Routine Identification of the Facial Nerve Using Electrical Stimulation During Otological and Neurotological Surgery," accessed via www.silversteininstitute.com, Dec. 2005; 1 pg.

(Continued)

*Primary Examiner* — Ryan Severson
(74) *Attorney, Agent, or Firm* — Dicke, Billig & Czaja, PLLC

(57) ABSTRACT

A surgical cutting instrument for use with a drive motor, and related system and method, is described. The surgical cutting instrument includes an elongated drive member, a cutting tip secured to the drive member, a non-conductive coupling body adapted for connection to a motor assembly, a housing maintaining the coupling body, a fluid coupling assembly and an electrical connector for connection to a stimulating energy source. The electrical connector is in electrical communication with the cutting tip via an electrical pathway.

34 Claims, 7 Drawing Sheets

U.S. PATENT DOCUMENTS

| | | | |
|---|---|---|---|
| 6,523,070 | B1 | 2/2003 | Stapleton et al. |
| 6,796,985 | B2 | 9/2004 | Bolger et al. |
| 2001/0031950 | A1 | 10/2001 | Ryan |
| 2002/0161372 | A1 | 10/2002 | Bolger et al. |
| 2004/0022602 | A1 | 2/2004 | Singh et al. |
| 2004/0122482 | A1 | 6/2004 | Tung et al. |
| 2004/0158169 | A1 | 8/2004 | Lewallen et al. |
| 2004/0260357 | A1 | 12/2004 | Vaughan et al. |
| 2004/0260358 | A1 | 12/2004 | Vaughan et al. |
| 2005/0004623 | A1 | 1/2005 | Miles et al. |
| 2005/0096649 | A1 | 5/2005 | Adams |
| 2007/0100334 | A1 | 5/2007 | McFarlin et al. |
| 2007/0162062 | A1 | 7/2007 | Norton et al. |

FOREIGN PATENT DOCUMENTS

| | | |
|---|---|---|
| WO | 2006/086367 A1 | 8/2006 |

OTHER PUBLICATIONS

H. Silverstein, Otolaryngology—Head and Neck Surgery article entitled "Adaptor for Continuous Stimulation (SACS) with the WR-S8 Monitor-Stimulator," Sep. 1990; 103(3); pp. 493-496.

Turk Otolarengoloji article entitled "Continuous Stimulation Monitoring of the Facial Nerve," Feb. 2001; pp. 251-254.

PCT Search Report mailed Jan. 25, 2008; 15 pgs.

INSTRUMENT AND SYSTEM FOR SURGICAL CUTTING AND EVOKED POTENTIAL MONITORING

CROSS-REFERENCE TO RELATED APPLICATIONS

This application is a continuation of U.S. patent application Ser. No. 11/260,503, filed Oct. 27, 2005 and entitled "Instrument And System For Surgical Cutting And Evoked Potential Monitoring."

BACKGROUND

The present invention relates to surgical cutting and surgical cutting instruments. More particularly, aspects relate to surgical cutting instruments and systems capable of both high-speed cutting and, in some embodiments electrical probing or evoked potential monitoring functions, as well as procedures utilizing such a device.

Surgical cutting instruments are commonly used to perform a variety of procedures. For example, many neurotological surgical operations involve partial or total removal of bone or other hard tissue via a high-speed rotating bur or other cutting tips. Exemplary procedures in this field include cochleostomies, removal of acoustic neuroma tumors, and removal of the scutum in a tympanoplasty. Numerous other surgical operations have similar bone/hard tissue cutting or removal requirements. The typical surgical cutting instrument is akin to a drill, including a drill handpiece that rotates a cutting implement. The handpiece houses a motor and a chuck or other adapter, with the chuck being rotated by the motor under the control of a foot-operated or finger-operated switch.

Human nerves are often in close proximity to an area of bone or tissue removal in many surgical procedures. Thus, one overarching concern relating to these types of surgical cutting operations and instruments is the danger of severing or otherwise damaging nerves through inadvertent cutting or excessive heat. For example, when a straight bur cutting instrument is used for bulk bone removal, a surgeon might be concerned with over-aggressive cutting as well as wobble and associated nerve damage. As another example, a curved bur cutting instrument used in finer cutting applications might have a high thermal discharge at the cutting bur giving rise to nerve damage concerns.

Indeed, often times the above-described surgical cutting instruments require additional steps and instruments for measuring nerve location to complete a surgical procedure. For example, a mastoidectomy can entail exposing the mastoid-periostiem and then carefully drilling/removing the mastoid bone using a cutting instrument and microscope. Moreover, a patient may have abnormal anatomy due to congenital or iatrogenic defects that places nerves in unanticipated regions such that the anatomical landmarks a surgeon might otherwise normally refer to as a guide for neural tissue may not exist. While carrying out such procedures, a surgeon can be required to sequentially cut with a surgical cutting instrument and then probe a cut area for nerves with a separate evoked potential monitoring system handpiece. This is clearly time-consuming and thus undesirable.

SUMMARY

Embodiments of the present invention relate to a surgical cutting instrument for use with a motor assembly having a motor and a drive mechanism. The cutting instrument includes an elongate drive member defining a proximal section and a distal section, a cutting tip secured to the distal section of the drive member, and a non-conductive coupling body adapted for connection to a motor assembly drive mechanism, the coupling body secured to the proximal section of the drive member. The instrument also includes a housing maintaining the coupling body and the proximal section of the drive member, a fluid coupling assembly in fluid communication with the drive member, and an electrical connector for connection to a stimulating energy source. In particular, the electrical connector is in electrical communication with the cutting tip via an electrical pathway established by at least the drive member and the fluid coupling assembly.

Other embodiments of the present invention relate to a surgical cutting system including a surgical cutting instrument, a motor assembly, and an evoked potential monitor system. The surgical cutting instrument includes an elongate drive member, a cutting tip, a non-conductive coupling body, a housing, a fluid coupling assembly and an electrical connector in electrical communication with the cutting tip via an electrical pathway. The motor assembly includes a drive motor and a drive mechanism driven by the motor. The coupling body and the drive mechanism are configured to releasably mount to one another. The coupling body electrically isolates the drive mechanism from the cutting tip electrical pathway upon mounting of the cutting instrument to the motor assembly. The evoked potential monitor system includes an energy source selectively electrically coupled to the cutting tip via the electrical connector for applying a stimulating energy to the cutting tip via the electrical connector and the electrical pathway.

Yet other embodiments of the present invention relate to a method of performing a surgical cutting procedure including providing a surgical cutting instrument having an elongate drive member, a cutting tip, a non-conductive coupling body, a housing, a fluid coupling assembly and an electrical connector electrically connected to the cutting tip via an electrical pathway. A motor assembly is coupled to the coupling body. An evoked potential monitoring system is connected to the cutting instrument via the electrical connector such that an energy source of the evoked potential monitor system is in electrical communication with the cutting tip. The motor assembly is operated to effectuate performance of a cutting operation with the cutting tip. A stimulation energy is applied to the cutting tip to facilitate detecting a proximity of the cutting tip to a nerve by the evoked potential monitor system.

DETAILED DESCRIPTION

Figure 1:
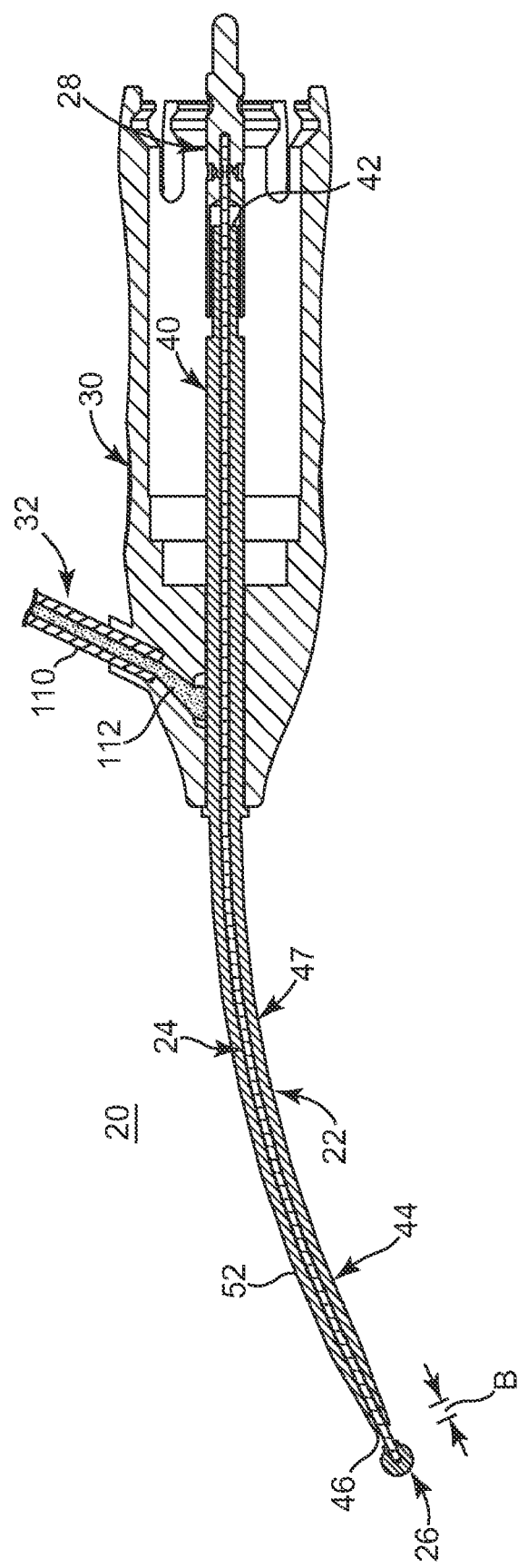
FIG. 1 is a cross-sectional view of one embodiment surgical cutting instrument in accordance with principles of the present invention.
Figure 2:
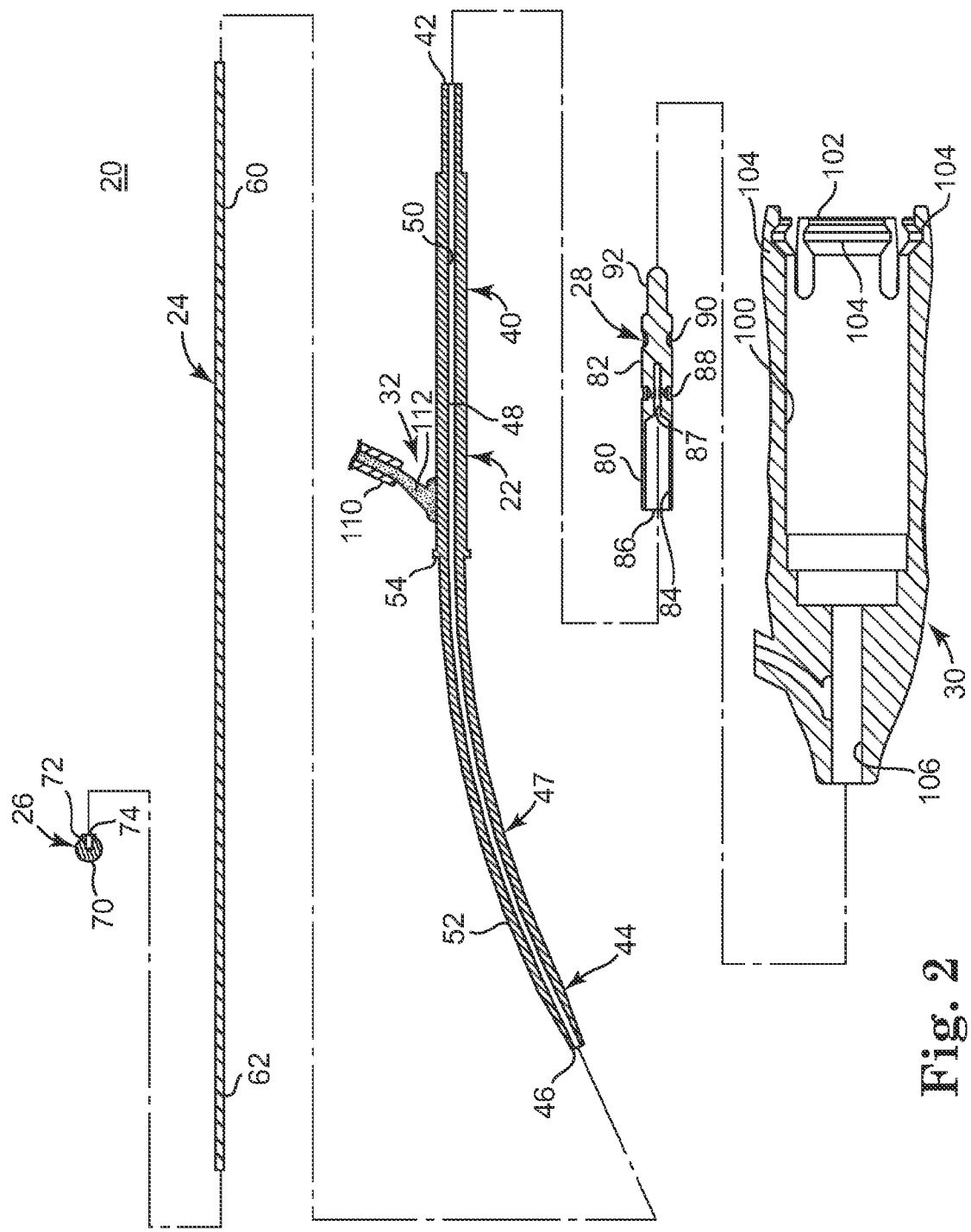
FIG. 2 is an exploded, cross-section view of the surgical cutting instrument of FIG. 1.

One embodiment of a surgical cutting instrument 20 is shown in FIGS. 1 and 2. The surgical cutting instrument 20 includes an outer support tube 22, an elongate drive member 24, a cutting tip 26, a coupling body (e.g., a tang) 28, a housing 30, and an electrical connector 32. In general terms, the elongate drive member 24 is coaxially disposed within the outer support tube 22. The cutting tip 26 is connected to and extends distally from the elongate drive member 24. The coupling body 28 is secured to the elongate drive member 24. The housing 30 maintains the outer support tube 22 and the coupling body 28. The electrical connector 32 delivers electrical energy from a source (not shown) to the cutting tip 26 via an electrical pathway established, at least in part, by the drive member 24, with the coupling body 28 electrically isolating the electrical pathway from components (e.g., a motor assembly) otherwise proximally mounted to the coupling body 28.

In some embodiments, a journal bearing is established between the elongate drive member 24 and the outer tube 22 upon rotation of the elongate drive member 24 relative to the outer tube 22 (e.g., via a motor assembly (not shown)). In some embodiments, the surgical cutting instrument 20 and components thereof provide one or more features that facilitate extremely high rotational speeds (on the order of 80,000 RPM), with the outer tube 22, and thus the elongate drive member 24, defining one or more curved segments where desired. U.S. application Ser. No. 10/776,835 (filed Feb. 11, 2004 and entitled "High Speed Surgical Cutting Instrument"), the teachings of which are incorporated herein by reference, describes examples of such features in accordance with one embodiment.

The outer tube 22 is an elongate tubular body, defining a proximal region 40 terminating at a proximal end 42, a distal region 44 terminating at a distal end 46, and an intermediate region 47 between the proximal and distal regions 40, 44. Further, the outer tube 22 defines a lumen 48 (best shown in FIG. 2) extending from the proximal end 42 to the distal end 46. Thus, an inner surface 50 of the outer tube 22 forms the lumen 48.

The outer tube 22 can assume a variety of longitudinal shapes. As shown at 52 in FIG. 1, in one embodiment, the outer tube 22 includes a curved segment at or along one or both of the intermediate region 47 and/or the distal region 44. In addition, the outer tube 22 is constructed to facilitate formation of a rotating journal bearing (i.e., frictional sliding journal bearing) relative to the elongate drive member 24 in the embodiment shown in FIG. 1. As will be described in greater detail below, the outer tube 22 acts as a part of an electrical pathway in some embodiments of the present invention. As such, at least a portion of the outer tube 22 is constructed of an electrically conductive material such that the outer tube 22 is capable of being in electrical communication with the elongate drive member 24 and the electrical connector 32. The outer tube 22 is also constructed of a material selected to provide the outer tube 22 with high strength, high stiffness characteristics satisfying dimensional and curvature constraints as desired. In one embodiment, the outer tube 22 is made of conventional surgical instrument materials, such as stainless steel.

Returning to FIG. 2, the elongate drive member 24 includes a proximal section 60 and a distal section 62. The elongate drive member 24 has an overall longitudinal length greater than the outer tube 22 such that, upon final assembly, the proximal and distal sections 60, 62 extend from the ends 42, 46, respectively, of the outer tube 22. The elongate drive member 24 is also constructed to be relatively thin. In particular, the thinness of the elongate member 24, in combination with the absence of a ball bearing assembly as part of the instrument 20, allows the lumen 48 to have a relatively small diameter, such that even with a preferred, minimized outer diameter, the outer tube 22 can have sufficient thickness to provide requisite stiffness when an appropriate material (e.g., 17-4 stainless steel) is selected for the outer tube 22.

In one embodiment, the elongate drive member 24 is also constructed to facilitate a rotating journal bearing relative to the outer tube 22 while maintaining structural integrity along a curved axial length. In particular, the elongate drive member 24 is formed to exhibit high strength and good fatigue characteristics. Additionally, at least a portion of the elongate drive member 24 is made of a conductive material to facilitate electrical communication between the outer support tube 22, the elongate drive member 24, and, as will be described in greater detail below, the cutting tip 26. Thus, in one embodiment, the elongate drive member 24 is formed of M2 hardened tool steel. Alternatively, other materials exhibiting the desired durability, fracture resistance, electrical conductivity, etc., can be employed for the elongate drive member 24.

Assembly of the surgical cutting instrument 20 is described in greater detail below. With respect to assembly of the outer tube 22 and the elongate drive member 24, however, a lubricant (not shown) is preferably provided along a length of the interface between the two components 22, 24 to facilitate formation of a hydrodynamic journal bearing therebetween. The elongate drive member 24 effectively "floats" relative to the outer tube 22 upon rotation of the elongate drive member 24 as it is supported by a hydrodynamic effect. As described in greater detail below, intimate contact between the outer tube 22 and the drive member 24 ensures that the desired electrical pathway is constantly maintained between the components 22, 24, such that the lubricant need not necessarily be electrically conductive. In another embodiment, the lubricant is electrically conductive and further facilitates electrical communication between the outer tube 22 and the elongate drive member 24. Thus, in one embodiment the lubricant is an electrically conductive grease lubricant, such as a lubricant available from Nye Lubricants of Fairhaven, Mass., under the trade name Nyogel 756G. However, in light of this description, it should be understood that other conductive lubricant materials can be employed.

The cutting tip 26 can assume a variety of forms, and in one embodiment includes a cutting bur 70 and an attachment end 72. The attachment end 72 is sized to receive the distal section 62 of the elongate drive member 24. To this end, the cutting tip 26 can be secured to the distal section 62 of the elongate drive member 24 via a number of known processes such as, for example, welding, braising, press-fitting, thermal shrink fitting, adhesive, etc. Alternatively, the elongate drive member 24 and the cutting tip 26 can be integrally formed such as by machining the elongate drive member 24 and the cutting tip 26 from a single piece of stock material. Regardless, the elongate drive member 24 and the cutting tip 26 should be secured in a manner to facilitate electrical communication between the two components 24, 26. As such, the cutting tip 26 is formed of electrically conductive material, such as nickel alloy materials in one embodiment. While the cutting tip 26 might include such cutting structures as small diamond burs, it should be understood that the spaces between such structures and the tissue and fluid associated with cutting operations allow an electrical interface between a cutting area (not shown) and conductive portions of the cutting tip 26. Regardless, the overall form of the cutting bur 70 can assume a variety of shapes and sizes known in the art (e.g., 2 mm fluted, 1 mm diamond, etc.). Alternatively, the cutting tip 26 can assume any other form appropriate for tissue and/or bone cutting procedures.

The coupling body 28 can assume a variety of forms but is generally configured to facilitate connection of a motor assembly (not shown) to the elongate drive member 24. As will be understood in greater detail below, some embodiments of the present invention require that the motor assembly be electrically insulated from the elongate drive member 24. In one such embodiment, the coupling body 28 is formed of a non-conductive material in order to ensure that the motor assembly is electrically insulated from the elongate drive member 24. For example, in one embodiment the coupling body 28 is formed of non-conductive ceramic or plastic material, such as an Ultem® resin available from GE Plastics of Pittsfield, Mass. or other polymeric or ceramic materials exhibiting similar tensile strength. Alternatively, the coupling body 28 can be formed from metal/metal alloy with a thin, non-conductive exterior coating.

It should be understood that the motor assembly (not shown) can be of the type typically employed with surgical cutting instruments, such as electric, battery-powered, or pneumatic. One exemplary motor assembly is available from Medtronic-Xomed of Jacksonville, Fla. under the trade name Visao®. Alternatively, other types of motors or drill drive systems can be employed. In general terms, the motor assembly includes a housing maintaining a drive motor. The motor drives (e.g., rotates) a shaft or other drive mechanism that is connected to the elongate drive member 24 upon mounting of the cutting instrument 20 to the motor assembly. To this end, the drive mechanism can include a connector of a type typically employed with surgical cutting instruments that facilitates connection or coupling to the cutting device, such as a mechanical connector (e.g., the drive mechanism can include a chuck extending from a motor-driven shaft opposite the drive motor), non-contacting air-driven coupling, etc. With this in mind the coupling body 28 of FIGS. 1 and 2 is adapted for use with a mechanical-type drive mechanism connector (e.g., chuck) for selective mounting of the coupling body 28 to the drive mechanism, with the coupling body 28 electrically isolating the drive mechanism, and thus the motor, from the elongate drive member 24.

In more specific terms, and in one embodiment, the coupling body 28 is defined by a distal portion 80 and a proximal portion 82. The distal portion 80 forms a first passage 84 extending from a distal end 86 thereof. The first passage 84 defines a diameter sized to loosely receive the proximal end 42 of the outer tube 22, serving to generally align the outer tube 22 relative to the proximal portion 82. Importantly, the distal portion 80 can rotate freely about the outer tube 22. The proximal portion 82 forms a second passage 87 extending proximally from the first passage 84. The second passage 87 is sized to receive and maintain the proximal section 60 of the elongate drive member 24. In this regard, the coupling body 28 can be further secured to the proximal section 60 of the elongate drive member 24 by a variety of techniques. For example, the coupling body 28 can be over-molded onto the elongate drive member 24. However, in one embodiment, the coupling body 28 is further secured to the proximal section 60 of the elongate drive member 24 by an epoxy, such as Loctite® M-31CL™ available from Henkel Loctite Corp. Alternatively, other epoxies or adhesives can be used.

The proximal portion 82 of the coupling body 28 forms a groove 90 and a tang 92 each adapted to facilitate coupling to the motor assembly drive mechanism (not shown), for example a chuck. The tang 92 serves as a guide surface that promotes rapid, consistent assembly of the drive mechanism to the coupling body 28. Once again, however, the coupling body 28 can assume a variety of other configurations.

Similar to the coupling body 28, the housing 30 can assume a variety of forms and is generally configured to support the outer tube 22 as well as facilitate attachment of the coupling body 28, and elongate drive member 24, to a motor assembly or "handpiece" (not shown). The instrument housing 30 is provided apart from any housing associated with the motor assembly/handpiece. In one embodiment, the housing 30 is formed from a non-conductive material such that the housing 30 also facilitates electrical isolation of the motor assembly from the elongate drive member 24, and in particular from the cutting tip 26, upon assembly of the cutting instrument 20 to the motor assembly. For example, in one embodiment the housing 30 is formed of a liquid crystal polymer. To this end, the housing 30 can be insert molded over the outer tube 22. Alternatively, a variety of other assembly techniques, such as gluing, welding, press fitting, thermal shrink fitting, etc., are equally acceptable. The housing 30 can incorporate a variety of features that facilitate mounting to the motor assembly. In one embodiment, the housing 30 forms a central aperture 100 having an open proximal end 102 defined by a plurality of spaced fingers 104. The central aperture 100 is sized to receive at least a portion of the motor assembly (e.g., a collet otherwise maintaining a chuck portion of the motor assembly drive mechanism), with the fingers 104 serving to capture the motor assembly within the aperture 100. In addition, or alternatively, the housing 30 can be configured to facilitate attachment to the motor assembly via snap fit, threads, interference fit, etc. Further, with the embodiments of FIGS. 1 and 2, the housing 30 defines a passage 106 fluidly connected to the aperture 100. The passage 106 is sized to maintain the outer tube 22 and can be formed during an insert molding procedure.

The electrical connector 32 includes an insulated wire 110 having an exposed end 112. For purposes of clarity, the size of the wire 110 is exaggerated in FIGS. 1 and 2. As shown in FIG. 1, the exposed end 112 is soldered to an outer surface of the outer support tube 22, with a distal portion of the wire being supported by the housing 30. However, in alternative embodiments, the electrical connector 32 can be welded, attached with a metal connector (e.g., screw), press fitted, crimped, or attached with conductive adhesive to the outer support tube 22 or integrally formed therewith. In general terms, the electrical connector 32, and in particular the wire 110, can be electrically connected to any point along a length of the outer tube 22; however, the area nearest the housing 30 or encompassed within the housing 30 is most ergonomical.

The surgical cutting instrument 20 is assembled by coaxially disposing the elongate drive member 24 within the lumen 48 of the outer tube 22. As previously described, in one embodiment a grease lubricant (not shown) is disposed along at least a portion of, preferably an entirety of, an interface between the elongate drive member 24 and the inner surface 50 of the outer tube 22. The outer tube 22 is assembled to the housing 30 as shown in FIG. 1, with the intermediate region 47 and the distal region 44 extending distal to the housing 30. As mentioned, in one embodiment, the insulated wire 110 of the electrical connector 32 is in electrical communication with the outer tube 22 as it is soldered to a portion of the outer tube 22.

The housing 30 can be insert molded over both the outer tube 22 and a portion of the electrical connector 32 extending from the outer tube 22, with the elongate drive member 24 then being placed within the lumen 48. Additionally, in one embodiment, an exterior non-conductive coating or sleeve (not shown) is formed or provided over the outer tube 22 distal the housing 30. For example, in one embodiment, a non-conductive sleeve (e.g., a shrink tube of polyester) is fitted about an exterior portion of the outer tube 22 otherwise extending distally from the housing 30 to the distal end 46. As will be understood in greater detail below, the non-conductive coating or sleeve promotes the ability of the cutting tip 26 to act as an electrical probe, preventing shunting of current to surrounding tissue, bone, or other structures when a stimulation energy is applied thereto (as might otherwise occur were the metal tube 22 left exteriorly "exposed"). Additionally, in one embodiment, various preferred design features of the surgical cutting instrument 20, such as material selection and the resultant journal bearing, allow for only limited exposure of the elongate drive member 24 distal to the distal end 46 of the outer tube 22, represented at B in FIG. 1. For example, the exposed length B of the elongate drive member 24 is preferably not greater than 0.1 inch (2.54 mm), and more preferably not greater than 0.05 inch (1.3 mm). In light of this disclosure, it should be understood that this limited exposure of the elongate drive member 24 (that is otherwise electrically conductive) to the environment can also promote more effective use of the cutting tip 26 as an electrical probe by reducing potential electrical shunting.

Regardless, the coupling body 28 is secured to the proximal section 60 of the elongate drive member 24, whereas the cutting tip 26 is attached to the distal section 62 of the elongate drive member 24. With this assembly, the insulated wire 110 of the electrical connector 32 is in electrical communication with the outer support tube 22, which in turn is in electrical communication with the elongate drive member 24, which in turn is in electrical communication with the cutting tip 26. This forms an electrical pathway consisting of the electrical connector 32, the outer support tube 22, the elongate drive member 24, and the cutting tip 26.

As alluded to above, the instrument 20 provides an extremely stable electrical pathway between the electrical connector 32 and the cutting tip 26. In one embodiment, intimate contact between the outer tube 22 and the elongate drive member 24 (due, at least in part, to the bend) establishes and consistently maintains the continuous electrical coupling between the two components 22, 24, such that any lubricant provided between the outer tube 22 and the drive member 24 need not be electrically conductive. In alternative embodiments, the use of an electrically conductive grease for the journal bearing acts to further maintain continuous electrical communication between the outer support tube 22 and the elongate drive member 24. Regardless, the journal bearing acts to maintain continuous electrical communication between the electrical connector 32 and the cutting tip 26 both at rest and during high-speed cutting operations, for example those reaching greater than 20,000 RPM, and in particular, those reaching approximately 80,000 RPM. In turn, the non-conductive coupling body 28 and non-conductive housing 30 act to insulate the motor assembly (not shown) from the electrical pathway to prevent interruption or misdirection of electrical current traveling through the electrical pathway to the cutting tip 26. This electrical isolation of the motor assembly is particularly important when the motor assembly (or handpiece) is grounded. In particular, it prevents current from being shunted away from the electrical pathway between the electrical connector 32 and the cutting tip 26.

In addition, by electrically isolating the patient-applied component (i.e., the cutting tip 26) from the motor assembly (not shown), the non-conductive coupling body 28 and housing 30 serve to prevent the conduction of any electrical or triboelectric noise from the motor assembly to the cutting tip 26 that might otherwise cause interference with other devices positioned near or at the surgical site that rely upon biosignals from the patient for proper operation. Thus, the cutting instrument 20 is highly compatible for use with other devices that amplify low-level biosigns such as EMG, EKG, EEG, ABR, etc., for the purpose of intraoperatively monitoring patient status. In fact, in alternative embodiments, the electrical conductor 32 can be eliminated, with the resultant cutting instrument providing a distinct improvement over existing designs when used in conjunction with a separate patient monitoring device.

Figure 3:
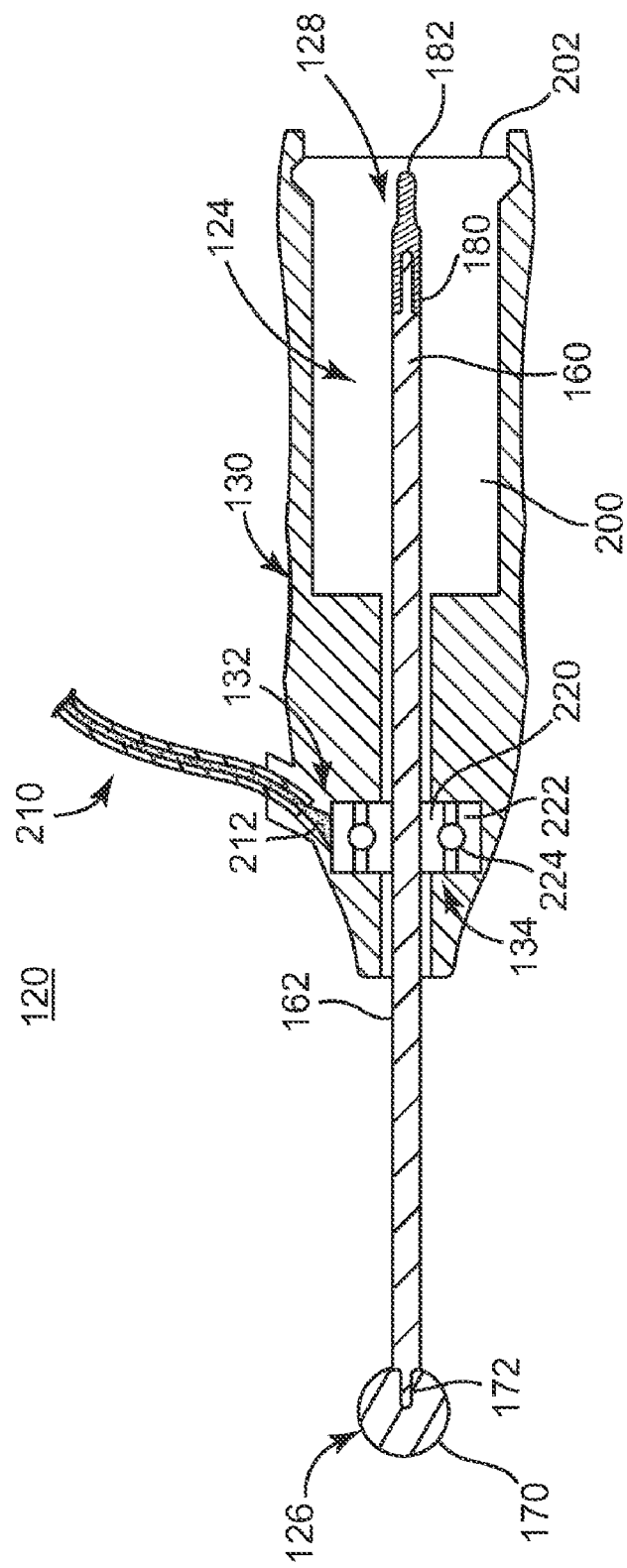
FIG. 3 is a cross-sectional view of another embodiment surgical cutting instrument in accordance with principles of the present invention.

While the surgical cutting instrument 20 has been described as providing a curved shaft configuration capable of high speed operation, in other embodiments, a more conventional straight shaft design can be employed and are capable of supporting larger shaft diameters and cutting tip diameters of 7 mm or greater (for example, for bulk bone removal procedures). For example, the surgical cutting instrument 20 can be formed with the outer tube 22, and thus the elongate drive member 24, assuming a straight or linear shape. Alternatively, FIG. 3 illustrates another embodiment surgical cutting instrument 120 in accordance with principles of the present invention that includes an elongate drive member 124, a cutting tip 126, a coupling body 128, a housing 130, an electrical connector 132, and a bearing assembly 134. The surgical cutting instrument 120 can be used as a "nose piece," similar to what is sometimes termed a "bur extender," that can be fitted on the front of a motor assembly or "handpiece" (not shown) to provide additional stability (e.g., to prevent wobble) to the elongate drive member 124 and cutting tip 126. In addition, and as described below, the surgical cutting instrument 120 is uniquely configured to establish an electrical pathway from the electrical connector 132 to the cutting tip 126.

In general terms of assembly and function, the elongate drive member 124 is coaxially disposed within the housing 130. The cutting tip 126 is connected to and extends distally from the elongate drive member 124. The coupling body 128 is secured to the elongate drive member 124 and is adapted for connection to a drive mechanism connector (not shown) of a motor assembly (not shown). The housing 130 is provided apart from the motor assembly, and maintains the electrical connector 132 and the bearing assembly 134. Thus, the housing 130 acts to maintain and support the elongate drive member 124 (as well as the cutting tip 126 secured thereto) and the bearing assembly 134. Finally, an electrical pathway is established from the electrical connector 132 to the cutting tip 126, for example via the bearing assembly 134 and the drive member 124. However, it should be noted that instead of the conductive coupling relationship shown, the cutting instrument 120 can be configured to establish an inductive or capacitive coupling to the cutting tip 126.

The elongate drive member 124 includes a proximal section 160 and a distal section 162. As shown, the elongate drive member 124 has an overall longitudinal length greater than that of the housing 130 such that upon final assembly, the distal section 162 extends from the housing 130. At least a portion of the elongate drive member 124 is formed of a conductive material in order to facilitate electrical communication with the cutting tip 126, as will be described in greater detail below. Some appropriate materials include stainless steel and tool steel materials, such as M-Series tool steels, A-Series tool steels, etc. Alternatively, other materials exhibiting the desired durability, fracture resistance, conductivity, etc., can be employed for the elongate drive member 124.

The coupling body 128 can assume a variety of forms, but is generally configured to facilitate connection of a motor assembly drive mechanism connector (not shown) to the elongate drive member 124. As a point of reference, the motor assembly (not shown) and the drive mechanism connector can assume a variety of forms (e.g., can include a chuck), as previously described in association with other embodiments. In one embodiment, the coupling body 128 is defined by a distal portion 180 and a proximal portion 182. The distal portion 180 of the coupling body 128 is configured to facilitate coupling of the elongate drive member 124 to the coupling body 128. The coupling body 128 can be secured to the proximal section 160 of the elongate drive member 124 by a variety of techniques, such as via adhesives, male and/or female threads, overmolding the coupling body 128 over the elongate drive member 124, and others. The proximal portion 182, in turn, is configured to serve as a guide surface that promotes rapid, consistent assembly of the motor assembly drive mechanism connector (e.g., a chuck) to the coupling body 128. Once again, however, the coupling body 128 can assume a variety of other forms, as can assembly of the coupling body 128 to the elongate drive member 124 and/or to the motor assembly drive mechanism.

Similar to other embodiments previously described, the coupling body 128 is formed of a non-conductive material and serves to assist in electrically isolating the elongate drive member 124 from the motor assembly (not shown). As such, the non-conductive coupling body 128 can be formed of a variety of non-conductive materials as previously described.

The cutting tip 126 can also assume a variety of forms, including those previously described. The cutting tip 126 includes a cutting bur 170 and an attachment end 172. The attachment end 172 is configured to receive the distal section 162 of the elongate drive member 124. To this end, the cutting tip 126 can be secured to the distal section 162 of the elongate drive member 124 via a number of known methods such as, for example, welding, braising, press-fitting, thermal shrink fitting, adhesive, male and/or female threads, etc. The elongate drive member 124 and the cutting tip 126 can alternatively be integrally formed such as by machining the elongate drive member 124 and the cutting tip 126 from a single piece of stock material. Additionally, the cutting bur 170 can assume a variety of shapes and sizes known in the art (e.g., 2 mm, 1 mm diamond, etc.). Regardless, the elongate drive member 124 and the cutting tip 126 are secured together such that they are in electrical communication, as previously described in association with other embodiments.

The housing 130 can assume a variety of forms and is generally configured to maintain the elongate drive member 124, the electrical connector 132, and the bearing assembly 134, as well as facilitate mounting of the cutting instrument 120 to a motor assembly (not shown). To this end, the housing 130 can be insert molded over a portion of the electrical connector 132 and the bearing assembly 134. Alternatively, a variety of other manufacturing techniques, such as gluing, welding, press-fitting, thermal shrink fitting, etc., are equally acceptable. The housing 130 can incorporate a variety of features that facilitate assembly to the motor assembly, including those previously described. For example, in one embodiment, the housing 130 forms a central aperture 200 having an open proximal end 202 configured for attachment to a corresponding component (e.g., a collet) of the motor assembly via methods known to those of ordinary skill in the art. The central aperture 200 is sized to receive and capture at least a portion of the motor assembly. In addition, or alternatively, the housing 130 can be configured to facilitate attachment to the motor assembly via snap fits, threads, interference fit, etc. In one embodiment, the housing 130 is formed of a non-conductive material (e.g., a liquid crystal polymer) to assist in electrically isolating the motor assembly from an electrical pathway formed by the cutting instrument 120 as described below.

The electrical connector 132 is configured to facilitate delivery of a stimulation energy from an energy source (not shown) to the cutting tip 126 via the electrical pathway. As such, in one embodiment, the electrical connector 132 includes insulated wire 210 having an exposed end 212. As will be described in greater detail below, the insulated wire 210 can be connected to monitoring systems, such as the energy source of a nerve monitoring system (not shown). As shown in FIG. 3, the insulated wire 210 has been overmolded into the housing 130, with the exposed end 212 in contact with the bearing assembly 134. In particular, the exposed end 212 is soldered or otherwise electrically coupled (e.g., metal fastener, conductive adhesive, crimping, press fit, etc.) to the bearing assembly 134. In other embodiments, the electrical connector 132 can establish an electrical pathway to the cutting tip 126 via other means. For example, the insulated wire 210 can be connected to a wire brush, such as a beryllium brush similar to those used in motor assemblies (not shown) that is in contact with the elongate drive member 124.

In one embodiment, the bearing assembly 134 is a ball bearing-type device, and includes an inner race or ring 220, an outer race or ring 222, and rolling elements (or ball bearings) 224, all of which are formed of electrically conductive material, such as stainless steel. The bearing assembly 134 can also include a bearing retainer ring, which need not be formed of electrically conductive material in some embodiments. The bearing assembly 134, and in particular the inner ring 220, defines a bore configured to coaxially receive the elongate drive member 124. It should be noted that the elongate drive member 124 is received within the inner ring 220 with sufficient intimacy to create a continuous electrical pathway between the two components 124, 220.

From the previous description, it will be understood that the bearing assembly 134 acts as an electrical pathway between the electrical connector 132 and the elongate drive member 124, such that the two are in electrical communication. It has been surprisingly found that passivated bearings, and bearings lubricated with non-conductive lubricant, or not otherwise lubricated, can interfere with forming an electrical pathway between the electrical connector 132 and the elongate drive member 124. For example, the bearing assembly 134 is designed with small gaps between the rolling elements 224 and the races 220, 222 that allow the rolling elements 224 to effectively float in instances of time during high-speed operation. Further, the rolling elements 224 may have eccentricities that result in selective contact between the rolling elements 224, the outer ring 222, and the inner ring 220. As such, in one embodiment, the bearing assembly 134 includes conductive grease (not shown) to fill gaps (not shown) between the rolling elements 224 and the inner ring 220 and the outer ring 222. As such, in one embodiment the bearing assembly is lubricated with a conductive grease, such as Nyogel® 756G available from Nye Lubricants of Fairhaven, Mass. As mentioned, passivation layers on the rolling elements 224, such as chromium oxide and/or nickel oxide, are often used to increase corrosion resistance and hardness of the rolling elements, but can serve to render them electrically non-conductive. As such, in one embodiment the rolling elements 224 are formed of non-passivated, stainless steel. Importantly, it has been found that by incorporating such features, the bearing assembly 134 is capable of forming a continuous electrical pathway, or continuous electrical communication, with the elongate drive member 124 and the electrical connector 132 while the cutting tip 126 is at rest and while it is turning at relatively high rotational speeds greater than 20,000 RPM, and in one embodiment at speeds approaching 80,000 RPM.

Upon final assembly, a stable electrical pathway is established from the electrical connector 132 to the cutting tip 126. Conversely, the coupling body 128, as well as the housing 130, acts to electrically insulate motor assembly (not shown) from the electrical pathway described upon mounting of the cutting instrument 120 to the motor assembly. In sum, in one embodiment, the bearing assembly 134 includes materials and is configured such that the electrical pathway is continuously maintained during operation, without intermittent interruption, during high-speed rotation of the elongate drive member 124, such as at speeds greater than 20,000 RPM, and as high as 80,000 RPM. The non-conductive coupling body 128 electrically isolates the drive member 124 (that is otherwise part of the electrical pathway) from the corresponding component of the motor assembly drive mechanism to which the coupling body 128 is attached, whereas the non-conductive housing 130 (that otherwise is in contact with the electrical pathway) electrically isolates the cutting instruments 120 from corresponding component(s) of the motor assembly (e.g., motor assembly housing or collet) to which the instrument housing 130 is attached. Depending upon a desired distal extension of the elongate drive member 124 from the housing 130, the elongate drive member 124 can further include a non-conductive, exterior coating or sleeve to prevent shunting of electrical current away from the desired electrical pathway from the electrical connector 132 to the cutting tip 126 and/or inadvertent contact with the motor assembly.

In addition to ensuring a stable electrical pathway, the non-conductive coupling body 128 and housing 130 serve to isolate the cutting tip 126 from electrical or triboelectrical noise generated by a motor assembly (not shown) otherwise mounted to and rotating/driving the elongate drive member 124. Thus, similar to the surgical cutting element 20 (FIG. 1) previously described, in alternative embodiments, the surgical cutting instrument 120 need not include the electrical connector 132, with the resultant instrument preventing the transmission of electrical or triboelectrical noise to the cutting tip 126 in a manner that might otherwise interfere with proper operation of a separate intraoperative patient monitoring device.

Figure 4:
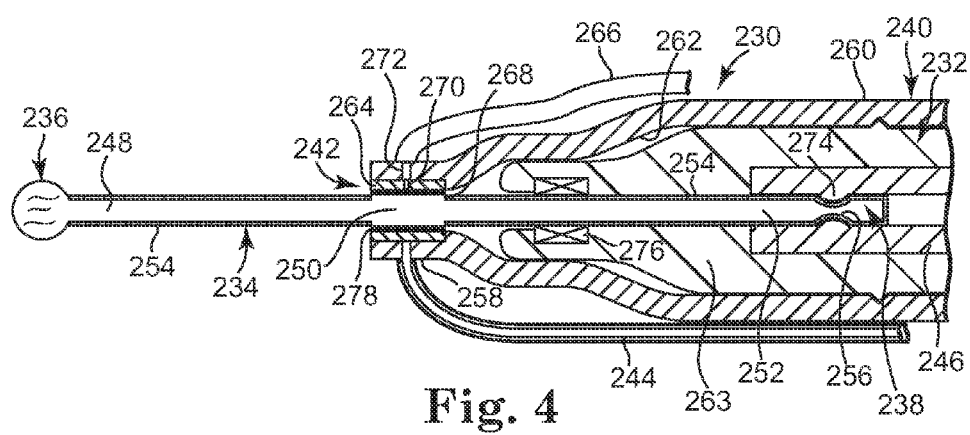
FIG. 4 is a cross-sectional view, including portions shown schematically, of another embodiment surgical cutting instrument in accordance with principles of the present invention in conjunction with a motor assembly.

A portion of another embodiment surgical cutting instrument 230 in accordance with principles of the present invention in conjunction with a portion of a motor assembly 232 is shown in FIG. 4. The instrument 230 includes an elongate drive member 234, a cutting tip 236, a coupling body 238, a housing 240, a fluid coupling assembly 242 (referenced generally), and an electrical connector 244. For ease of illustration, the drive member 234, the cutting tip 236, the coupling body 238 and portions of the motor assembly 232 are shown schematically in FIG. 4. As described below, the instrument 230 operates in a manner similar to previous embodiments, whereby the coupling body 238 is coupled to the motor assembly 232 (such as via a chuck 246) for rotating the cutting tip 236. Further, a stimulating current delivered by the electrical connector 244 flows to the cutting tip 236 via the fluid coupling assembly 242 as part of an evoked potential monitoring operation.

The drive member 234 is formed of a rigid, electrically conductive material (e.g., steel), and defines a distal portion 248, an intermediate portion 250, and a proximal portion 252. The distal portion 248 is attached to or otherwise terminates at the cutting tip 236 and thus defines an axial length or extension of the cutting tip 236 relative to the housing 240, and can assume a variety of lengths. The proximal portion 252 terminates, or in one embodiment (as shown) forms, the coupling body 238. Regardless, in one embodiment, the intermediate portion 250 has an increased outer diameter as compared to the distal and proximal portions 248, 252 (at least in those regions immediately adjacent the intermediate portion 250), and is characterized as being exteriorly exposed as compared to the distal and proximal portions 248, 252. More particularly, in one embodiment an exterior of the drive member 234 is encompassed by an electrically non-conductive, insulating coating 254 (referenced generally) in all regions except the intermediate portion 250. As a point of reference, a thickness of the insulating coating 254 is exaggerated in FIG. 4 for clarity purposes. With embodiments in which the drive member 234 forms the coupling body 238, the coupling body 238 is also covered by the coating 254 (it being understood that for alternative embodiments in which the coupling body 238 is formed apart from, and subsequently attached to, the drive member 234, the coupling body 238 is either comprised of an electrically non-conductive material and/or is coated with an electrically insulative covering). Conversely, with embodiments in which the drive member 234 forms the cutting tip 236, the cutting tip 236 is free of the insulative coating 254. Regardless, the insulative coating 254 can take a variety of forms and can be applied in a multitude of manners. For example, the insulative coating 254 can be plastic shrink tubing, over molded plastic, etc., formed of an electrically non-conductive material.

The cutting tip 236 and the coupling body 238 can assume any of the forms previously described. Thus, the cutting tip 236 can be a bur, cutting teeth, etc. As alluded to above, the coupling body 238 can be integrally formed by the drive member 234 or provided separately. In one embodiment, however, the coupling body 238 forms a groove 256 for releasably engaging the chuck 246. Alternatively, the coupling body 238 can assume other configurations commensurate with a corresponding component of the motor assembly 232.

The housing 240 can incorporate various features previously described and is formed from, or exteriorly coated with, an electrically non-conductive material (e.g., the housing 240 can be formed of electrically insulative plastic). The housing 240 defines a distal region 258, a proximal region 260, and a central passage 262. The passage 262 along the proximal region 260 is sized to matingly receive a corresponding housing 263 (illustrated schematically) of the motor assembly 232. Conversely, the distal region 258 forms the passage 262 to be slightly greater than a diameter of the drive member 234 and is configured to maintain portions of the fluid coupling assembly 242 as described below.

In one embodiment, the fluid coupling assembly 242 includes a conductive spacer 264 and tubing 266 fluidly connected to a source (not shown) of electrically conductive fluid. The conductive spacer 264 is formed of a hardened, electrically conductive metal and is mounted to the distal region 258 of the housing 240 about the passage 262. In one embodiment, the conductive spacer 264 is a ring or other cylindrical shape defining an internal aperture 268 (referenced generally). The internal aperture 268 has a diameter approximating an outer diameter of the intermediate portion 250 of the drive member 234 such that upon final assembly, the intermediate portion 250 is in approximate contact with the conductive spacer 264. In one embodiment, the conductive spacer 264 is porous and/or forms a radial opening(s) (one of which is illustrated at 270 in FIG. 4) for reasons described below.

The tubing 266 is formed of an electrically insulative material and is fluidly coupled at a proximal end (not shown) thereof to a source of electrically conductive fluid (not shown). For example, the electrically conductive fluid can be saline, etc. Regardless, a distal end of the tubing 266 is fluidly connected to the conductive spacer 264, such as via a port 272 formed in the housing 240. With this configuration, conductive fluid from the tubing 266 flows to the conductive spacer 264 and then to an interior surface thereof, due to either a porosity or other formed opening 270 in the conductive spacer 264 as previously described.

Finally, the electrical connector 244 is an insulated wire or other body capable of delivering an electrical current. The electrical connector 244 is electrically connected (e.g., welded) to the conductive spacer 264. Thus, a portion of the electrical connector 244 can extend through the housing 240 as shown.

During use, the cutting instrument 230 is mounted to the motor assembly 232 as shown. As a point of reference, the motor assembly 232 includes the chuck 246 forming an internal flange 274 nestable within the groove 256 of the coupling body 238 to facilitate engagement between the coupling body 238/chuck 246. Further, the motor assembly 232 can include bearings 276 (drawn schematically) for supporting the drive member 234 when rotated by driven rotation of the chuck 246/coupling body 238. Regardless, a stimulating current is delivered to the cutting tip 236 as part of an evoked potential monitoring operation (that may or may not occur in conjunction with cutting) by supplying a conductive fluid to the conductive spacer 264 via the tubing 266. Due to a porosity and/or other opening 270 in the conductive spacer 264, the conductive fluid flows to an interface or spacing between the conductive spacer 264 and the intermediate portion 250 of the drive member 234. As shown, a conductive fluid film 278 is formed, electrically coupling the conductive spacer 264 and the drive member 234. Where desired, seals (not shown) can be provided distal and/or proximal the conductive spacer 264 to contain the conductive fluid at the conductive spacer 264/drive member 234 interface. Regardless, an electrical pathway is established in which a stimulating current flows from electrical conductor 244 (otherwise electrically connected to a stimulating energy source (not shown)), through the conductive spacer 264 and the conductive fluid film 278, through the drive member 234, and to the cutting tip 236. The insulative coating 254 promotes use of the cutting tip 236 as an electrical probe, preventing shunting of current to surrounding tissue. Further, the insulative coating 254 over the coupling body 238 (or other, non-conductive configuration of the coupling body 238) in conjunction with the non-conductive housing 240 electrically isolates the conductive pathway described above from the motor assembly 232 as well as from a user otherwise handling the housing 240.

Figure 5A:
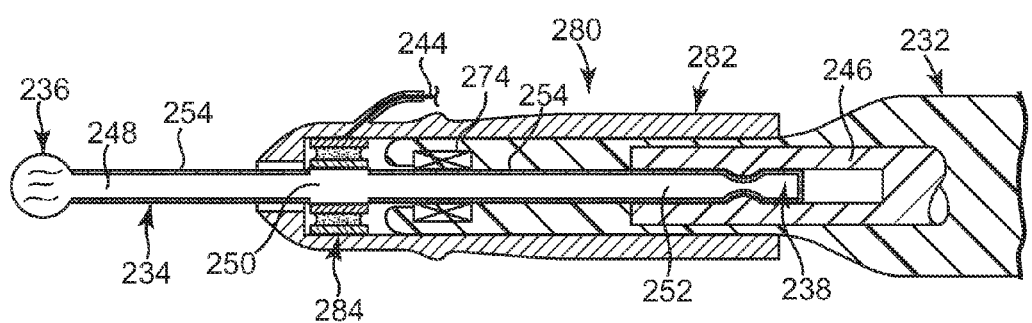
FIG. 5A is a cross-sectional view of another embodiment surgical cutting instrument in accordance with principles of the present invention in conjunction with a motor assembly.

A portion of another embodiment surgical cutting instrument 280 in accordance with the principles of the present invention in conjunction with a portion of the motor assembly 232 described above, is shown in FIG. 5A. The instrument 280 is similar in many respects to the instrument 230 (FIG. 4) previously described, with like elements having like reference numbers. With this in mind, the instrument 280 includes the elongate drive member 234, the cutting tip 236, the coupling body 238, a housing 282, an electrical coupling assembly 284 (referenced generally), and the electrical connector 244. As described below, the instrument 280 operates in a manner similar to previous embodiments, whereby the motor assembly 232 is coupled to the coupling body 238 (such as via the chuck 246) for rotating the cutting tip 236. Further, a stimulating current delivered by the electrical connector 244 (such as from a stimulating energy source (not shown)) flows to the cutting tip 236 via the electrical coupling assembly 284 as part of an evoked potential monitoring operation.

Similar to previous embodiments, the drive member 234 is formed of or coated with a rigid, electrically conductive material, and defines the distal portion 248, the intermediate portion 250, and the proximal portion 252. In this regard, the distal and proximal portions 248, 252 are encompassed or covered by the electrically non-conductive, insulating coating 254 (referenced generally) as previously described, whereas the intermediate portion 250 is exteriorly exposed.

The housing 282 is, similar to previous embodiments, formed of an electrically non-conductive material, such as plastic. In addition, the housing 282 is configured to receive and maintain the electrical coupling assembly 284, such as via a press fit. Alternatively, the housing 282 can include additional internal features that more securely receive and maintain the electrical coupling assembly 284.

Figure 5B:
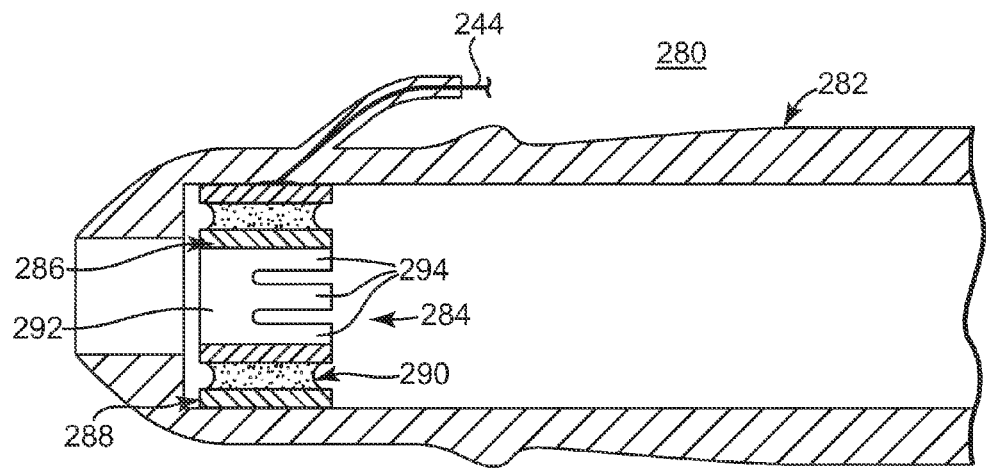
FIG. 5B is a cross-sectional view of a portion of the instrument of FIG. 5A.

With additional reference to FIG. 5B, the electrical coupling assembly 284 has a rotatable, bearing-type configuration, and includes an inner harness 286, an outer race 288, and a bearing body 290. The inner harness 286 is a generally ring-shaped body defining a base 292 and a plurality of fingers 294. The fingers 294 extend from the base 292 in a generally longitudinal fashion (relative to the longitudinal axis defined by the drive member 234), and combine to define an inner diameter approximating an outer diameter of the intermediate portion 250 of the drive member 234. Thus, upon final assembly, the fingers 294 contact and engage the intermediate portion 250 of the drive member 234. To ensure consistent, continuous contact, in one embodiment, the fingers 294 are "pre-loaded" to extend radially inwardly relative to the base 292, combining to naturally assume an inner diameter less than an outer diameter of the intermediate portion 250. Regardless, the inner harness 286 is formed of an electrically conductive metal, such as steel. The outer race 288 is similarly formed of a conductive metal, and is sized for securement to the housing 282 (e.g., press fit). Finally, the bearing body 290 is also electrically conductive, and is adapted to facilitate rotation of the inner harness 286 relative to the outer race 288. In one embodiment, the bearing body 290 is a ferro-fluid bearing. In addition, or as an alternative, the bearing body 290 can include one or more ball bearing(s) formed of an electrically conductive material (e.g., steel). Regardless, the electrical connector 244 includes an insulated wire electrically coupled (e.g., welded) to the outer race 288, and thus, can extend through a thickness of the housing 282. With this configuration, an electrical pathway is established from the electrical connector 244 to the cutting tip 236 via the electrical coupling assembly 284 and the drive member 234.

Returning to FIG. 5A, during use the instrument 280 is connected to the motor assembly 232. For example, the chuck 246 (shown schematically) is connected to the coupling body 238, with the bearings 274 (shown schematically) supporting the drive member 234 as previously described. Rotation of the chuck 246 causes the cutting tip 236 to rotate as part of a cutting operation. In addition, the instrument 280 can be employed to perform an evoked potential monitoring operation apart from and/or simultaneously with tissue cutting. A stimulating current is delivered via the electrical connector 244 to the electrical coupling assembly 284. In particular, the stimulating current is delivered to the outer race 288 which in turn conducts the current to the inner harness via the bearing assembly 290. Intimate contact between the inner harness 286 and the drive member 234 (regardless of whether the drive member 234 is rotating) conducts the applied current to the cutting tip 236. Once again, the insulative coating 254 prevents shunting of the current distal the housing 282, such that the current is focused upon the cutting tip 236. In addition, the insulative coating 254 (and/or other non-conductive features associated with the coupling body 238) and the housing 282 combine to insulate the motor assembly 232 from the current, as well as from a user otherwise handling the housing 282. In one embodiment, the housing 282/electrical coupling assembly 284 serves as a re-usable device, and thus can be repeatedly employed with a variety of other drive members 234 (and thus, cutting tip 236 and coupling body 238) configurations.

Figure 6:
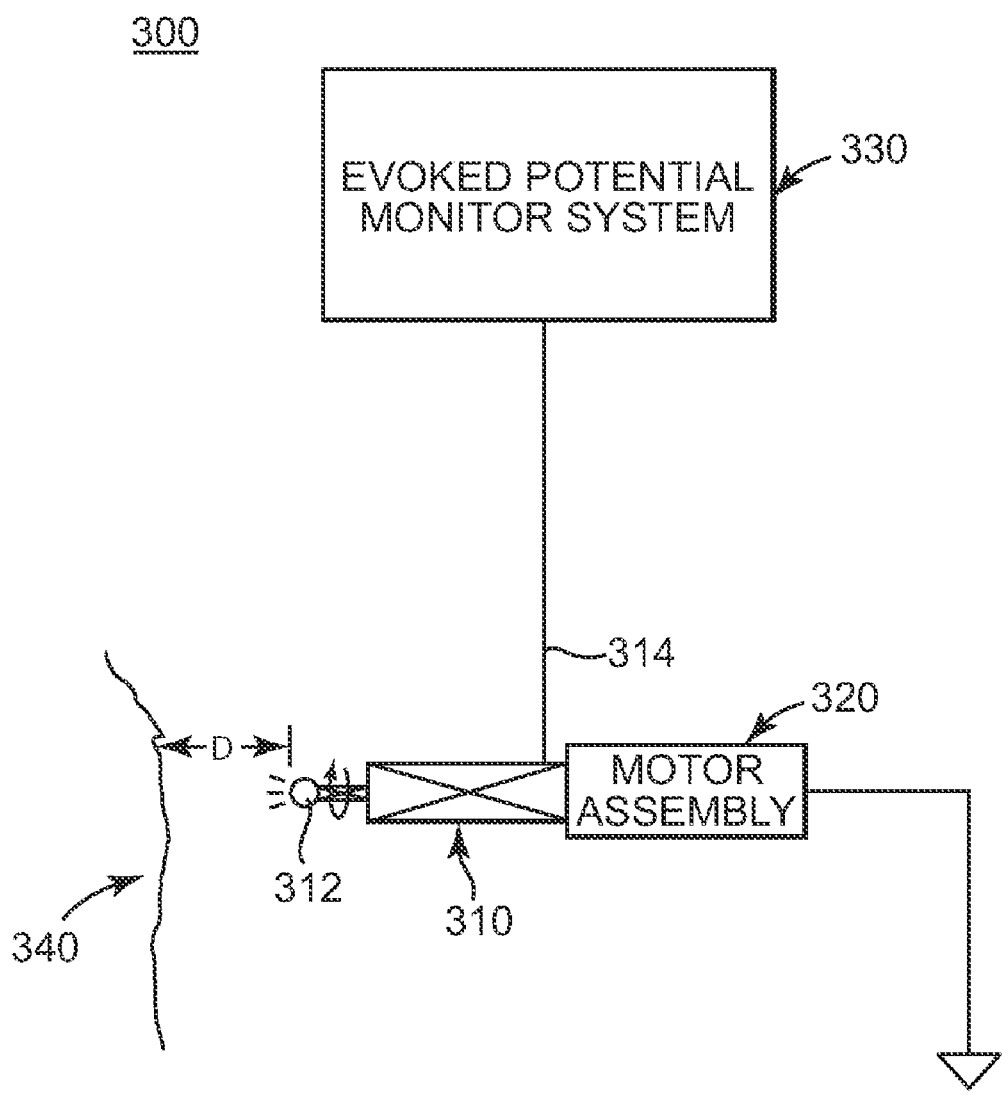
FIG. 6 is a schematic illustration of a surgical cutting system in accordance with principles of the present invention.

Regardless of an exact form of the surgical cutting instrument, a surgical cutting system can be provided in accordance with principles of the present invention. For example, FIG. 6 illustrates schematically a surgical cutting system 300 in accordance with one embodiment of the present invention. The surgical cutting system 300 includes a surgical cutting instrument 310, a motor assembly 320, and an evoked potential monitor (or monitoring) system 330. It has been discovered that the sequential and separate process of probing then cutting, or vice-versa, as has been required in the past, is an area of potential improvement addressed by the surgical cutting system 300, resulting, for example, in an early warning system for surgeons, alerting them to potential iatrogenic injury to neural tissue. The simultaneous cutting and probing procedure described below is safer for the patient (as compared to the conventional technique of alternating cutting and probing) as the surgeon is no longer required to manually estimate the appropriate depth of cut between probing operations, and overall procedure time is reduced.

In one embodiment, the surgical cutting instrument 310 can be of a similar design to the surgical cutting instruments 20 (FIG. 1), 120 (FIG. 3), 230 (FIG. 4), or 280 (FIG. 5A), previously described, and generally includes a cutting tip 312 and an electrical connector 314, with the electrical connector 314 being electrically connected to the cutting tip 312 via an electrical pathway established by the cutting instrument 310 as previously described. The motor assembly 320 can assume any known form, and though shown schematically, generally includes a housing, a motor and a drive mechanism/connector, with the surgical cutting instrument 310 and the motor assembly 320 adapted for mounting to one another as previously described. Regardless, the motor assembly 320 and the surgical cutting instrument 310 are assembled such that motor assembly 320 drives (e.g., rotates) the cutting tip 312 in order to perform a cutting operation. Notably, as described above, the motor assembly 320 is electrically isolated from the cutting tip 312 and the electrical pathway upon mounting of the cutting instrument 310 to the motor assembly 320.

The evoked potential monitor system 330 is a nerve integrity monitoring system, such as a NIM-Response® 2.0 nerve integrity monitoring system available from Medtronic-Xomed, Inc. of Jacksonville, Fla. In general terms, the evoked potential monitor system 330 is adapted to indicate when an energized probe, for example the cutting tip 312, is proximate a nerve 340 (shown schematically) during a surgical cutting procedure. For example, the evoked potential monitor system 330 can include a patient interface console maintaining circuitry and related equipment, the console being capable of providing a stimulating energy or current to a probe via a stimulating energy source provided as part of the system 330. In addition, electrodes (not shown) are placed on or in muscles that are enervated by nerves in proximity to the expected cutting area, and are electrically coupled to the interface console. In this manner, the electrodes signal a response to the patient interface console's internal equipment (e.g., processor) when a stimulating current enervates a nerve of concern. The evoked potential monitor system 330 can also include alarms or other indicators as known in the art. Regardless, the electrical connector 314 is in electrical communication with both the evoked potential monitor system 330 and the cutting tip 312 (via the electrical pathway). In this manner, the cutting tip 312 serves as an electrical probe in conjunction with the evoked potential monitor system 330 when energized via the electrical connector 314.

During use, the evoked potential monitor system 330 prompts delivery (preferably continuous delivery) of a stimulating energy (e.g., current) through the electrical connector 314 to the cutting tip 312 via the electrical pathway established by the cutting instrument 310. The previously described surgical cutting instruments 20 (FIG. 1), 120 (FIG. 3), 230 (FIG. 4), 280 (FIG. 5A) are several examples of instruments capable of ensuring that the stimulating energy is continuously delivered to the cutting tip 312. Properly placed patient electrodes (not shown) provide the evoked potential monitor system 330 with information indicative of a proximity of the cutting tip 312 to the nerve 340 in response to the applied stimulating current. For example, based on a comparison of the applied stimulating current with the signaled information from the patient electrodes, the evoked potential monitor system 330 can detect, and/or provide the user with information indicative of, the energized cutting tip 312 being at or within a distance D of the nerve(s) 340 of concern. The motor assembly 320, otherwise electrically isolated from the delivered stimulation energy, is simultaneously powered to rotate the cutting tip 312. Thus, simultaneous or substantially concurrent bone or tissue cutting and nerve probing functions can be performed by the system 300. Further, evoked potential monitoring can be performed via the cutting instrument 310 with the motor assembly 320 deactivated (i.e., "off" or not otherwise driving the cutting instrument 310).

Figure 7:
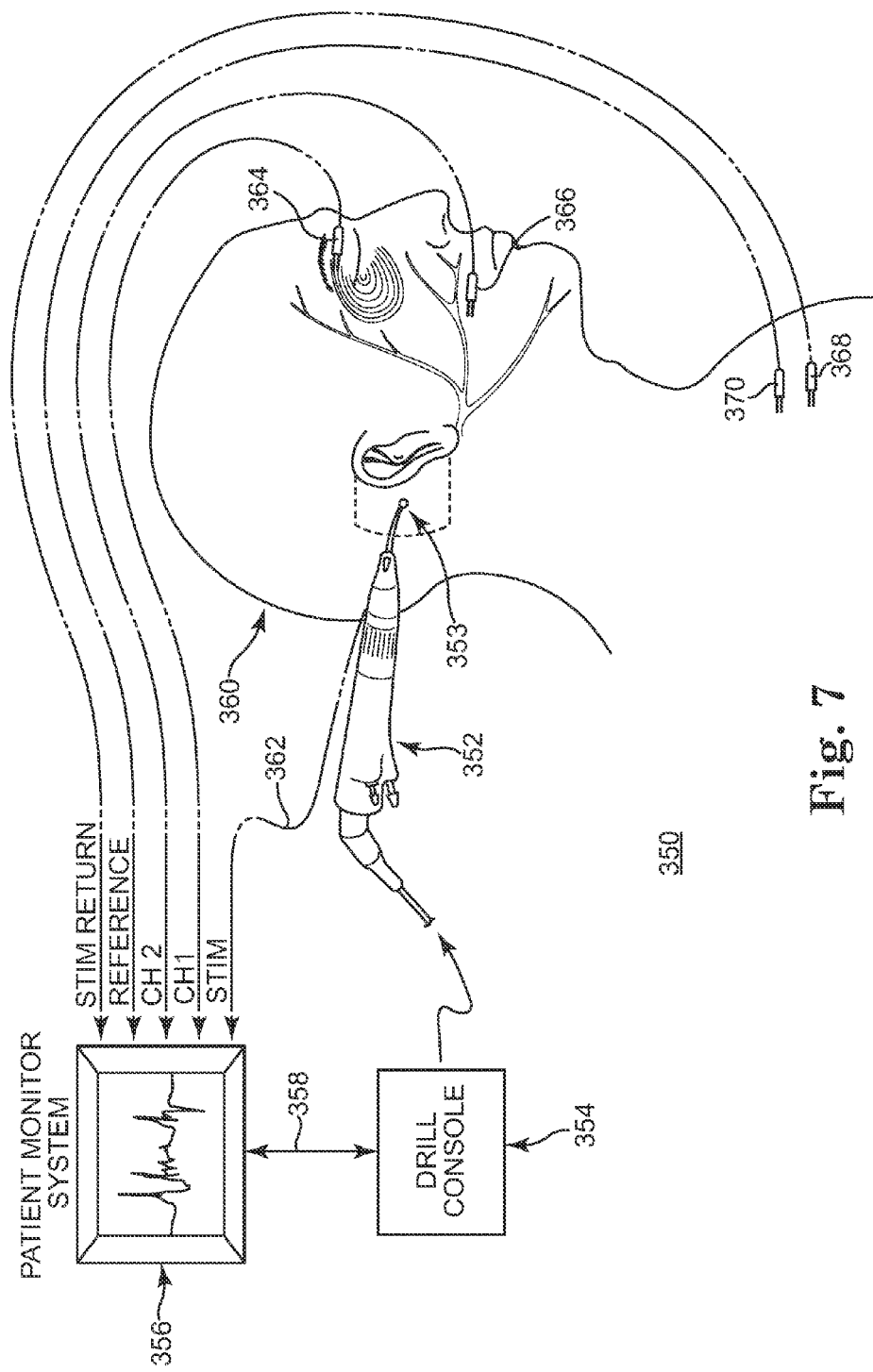
FIG. 7 is a schematic illustration of another surgical cutting system in accordance with principles of the present invention.

In a related embodiment surgical cutting system 350 shown in FIG. 7, a surgical cutting instrument 352 having a cutting tip 353 is again powered by a motor assembly (illustrated schematically in FIG. 7 as part of the cutting instrument 352). The surgical cutting instrument 352 can assume any of the forms previously described. The cutting instrument/motor assembly 352 is electronically coupled to a surgical drill console 354, such as an XPS® console (Medtronic-Xomed, Inc., of Jacksonville, Fla.), having internal circuitry for controlling power delivered to the motor assembly 352. The system 350 further includes a patient monitor system 356 such as an evoked potential monitor system as previously described or a surgical navigation platform such as an image guidance system available under the trade name LandmarX® Element IGS System from Medtronic-Xomed, Inc., of Jacksonville, Fla. Regardless of an exact configuration, a communication link 358 (wired or wireless connection) is established between the surgical drill console 354 and the patient monitoring system 356, with the patient monitor system 356 being adapted (e.g., processor operating pursuant to appropriate programming) to prompt the surgical drill console 354 to disable the motor assembly 352 via a signal delivered through the communication link 358.

More particularly, the patient monitoring system 356 is adapted to monitor a patient 360 during a surgical procedure involving the surgical cutting instrument 352. Patient monitoring can include evoked potential monitoring as previously described (e.g., a wire 362 can provide a stimulating current from the patient monitor system 356 to the cutting instrument 352), or can be any other appropriate type of monitoring (e.g., image guidance). For example, in one embodiment, the patient monitor system 356 includes EMG electrodes 364, 366 ("CH 1" and "CH 2"), along with a stimulation return path electrode 368 ("STIM RETURN") and a reference electrode 370 ("REFERENCE"). The EMG electrodes 364, 366 are placed in muscles innervated by the nerves of concern. The return path electrode 368 provides a return path for the stimulation current delivered by the cutting tip 353 for embodiments in which the delivered simulation current is an isolated output that is not Earth referenced (and therefore requires its own isolated return). The reference electrode 370 provides a common reference between the patient 360 and the patient monitor system 356 (required to center the EMG signal within the input range of the recording amplifiers). The return path and reference electrodes 368, 370 can be placed at a variety of locations on the patient 360, such as the sternum, shoulder, forehead, etc. Regardless, upon detecting or otherwise determining that the cutting tip 353 is proximate critical anatomy (e.g., nerve) of the patient 360, the patient monitor system 356 is adapted to deliver a disabling signal to the surgical drill console 354, prompting powering off of the cutting instrument/motor assembly 352. Thus, the system 350 effectively provides an automatic "kill-switch" to further ensure patient safety.

In light of the above, the advantages of non-sequential, high-speed cutting and probing or other monitoring can be realized in accordance with embodiments of the present invention. The surgical cutting instrument and related surgical cutting system can be employed to perform virtually any surgical procedure requiring cutting of tissue and nerve monitoring, and especially with those procedures in which a small diameter, bur-type cutting tip is rotated at elevated speeds (e.g., greater than 20,000 RPM) to effectuate desired tissue removal in an otherwise confined surgical access site. For example, the instrument and system of embodiments of the present invention can be employed to perform procedures such as mastoidectomy, discectomy, etc., to name but a few. Aspects of the present invention are not limited to any particular procedure, cutting tip style, or cutting speed. Regardless of the exact procedure, the instrument and system of embodiments of the present invention operate to provide both tissue cutting and evoked potential (i.e., nerve) monitoring without the need for a separate electrical probe instrument.

In alternative embodiments, the surgical cutting system includes one or more other biosignal-based patient monitoring devices (e.g., EMG, EKG, EEG, ABP, etc.) in addition to the surgical cutting instrument and the motor assembly. With these embodiments, the cutting system may or may not include an evoked potential monitor system, and the surgical cutting instrument may or may not include an electrical connector otherwise electrically connecting the cutting tip to an energy source. Regardless, non-conductive coupling body and housing components of the surgical cutting instrument can take any of the forms described to electrically isolate the motor assembly from the cutting tip. During use, the surgical cutting instrument is mounted to the motor assembly, and the motor assembly is operated to drive (e.g., rotate) the cutting tip at a surgical site. Concurrent with operation of the motor assembly, the patient monitoring device operates to monitor a condition of the patient. To this end, electrical or triboelectric noise generated by the motor assembly is not conducted to the cutting tip (and thus not conducted to the surgical site) due to the non-conductive coupling body and housing, and thus does not interfere with operation of the patient monitoring device(s).

Although specific embodiments have been illustrated and described herein, it will be appreciated by those of ordinary skill in the art that a variety of alternate and/or equivalent implementations may be substituted for the specific embodiments shown and described without departing from the scope of the present invention. This application is intended to cover any adaptations or variations of the specific embodiments discussed herein. Therefore, it is intended that this invention be limited only by the claims and the equivalents thereof.

What is claimed is:

1. A surgical cutting instrument for use with a motor assembly having a motor and a drive mechanism, the instrument comprising:
    an elongate drive member defining a proximal section and a distal section;
    a cutting tip secured to the distal section of the drive member;
    a non-conductive coupling body adapted for connection to a motor assembly drive mechanism, the coupling body secured to the proximal section of the drive member;
    a housing maintaining the coupling body and the proximal section of the drive member;
    a fluid coupling assembly in fluid communication with the drive member, the fluid coupling assembly adapted for fluid connection to a source of electrically conductive fluid; and
    an electrical connector in electrical communication with the cutting tip via an electrical pathway established by at least the drive member and the fluid coupling assembly, the electrical connector adapted for electrical connection to an energy source.

2. The cutting instrument of claim 1, wherein the non-conductive coupling body is formed of polymeric material.

3. The cutting instrument of claim 1, wherein the housing maintains a portion of the electrical connector.

4. The cutting instrument of claim 1, wherein the housing is formed of non-conductive material.

5. The cutting instrument of claim 1, wherein the cutting instrument is configured such that energy flowing through the electrical connector is continuously delivered to the cutting tip during rotation of the drive member at a rotational rate of at least 20,000 RPM.

6. The cutting instrument of claim 1, wherein the housing maintains a conductive spacer of the fluid coupling assembly, which is disposed between the housing and the elongate drive member, and further wherein the electrical connector is coupled to the conductive spacer such that the electrical pathway from the electrical connector to the tip includes the elongate drive member and the conductive spacer.

7. The cutting instrument of claim 6, wherein the conductive spacer is cylindrically shaped and includes an opening to allow the electrically conductive fluid to flow to the drive member.

8. The cutting instrument of claim 6, wherein the conductive spacer is porous to allow the electrically conductive fluid to flow to the drive member.

9. The cutting instrument of claim 8, wherein the cutting tip is a bur.

10. The cutting instrument of claim 6 further comprising:
    an outer tube maintained by the housing, the outer tube defining a proximal region terminating at a proximal end, a distal region terminating at a distal end, and a lumen extending from the proximal end to the distal end;

wherein the elongate drive member is disposed within the lumen of the outer tube and the conductive spacer is positioned between an inner surface of the outer tube and the elongate drive member.

11. The cutting instrument of claim 10, wherein an outer surface of the outer tube distal the housing is at least partially covered by a non-conductive material.

12. The cutting instrument of claim 10, wherein the fluid coupling assembly includes tubing adapted for carrying the electrically conductive fluid along an outer surface of the outer tube, the tubing fluidly coupled to the conductive spacer through a port in the outer tube.

13. The cutting instrument of claim 1, wherein the drive member is straight.

14. The cutting instrument of claim 1, wherein the electrically conductive fluid is saline.

15. A surgical cutting system comprising:
   a surgical cutting instrument, the cutting instrument including:
      an elongate drive member,
      a cutting tip attached to a distal section of the drive member,
      a non-conductive coupling body attached to a proximal section of the drive member,
      a housing maintaining the coupling body and the proximal section of the drive member,
      a fluid coupling assembly in fluid communication with the drive member, the fluid coupling assembly adapted for fluid connection to a source of electrically conductive fluid,
      an electrical connector in electrical communication with the cutting tip via an electrical pathway established by at least the drive member and the fluid coupling assembly;
   a motor assembly including a motor and a drive mechanism selectively mounted to the non-conductive coupling body such that the drive mechanism is electrically insulated from the electrical pathway, the motor adapted to rotate the drive member; and
   an evoked potential monitor system having an energy source selectively coupled to the electrical connector for applying a stimulating energy to the cutting tip via the electrical connector and the electrical pathway.

16. The surgical cutting system of claim 15, wherein the system is adapted such that as the motor rotates the cutting tip at speeds of at least 20,000 RPM, the stimulating energy is continuously delivered from the energy source to the cutting tip.

17. The surgical cutting system of claim 15, wherein the evoked potential monitor system is adapted to indicate when the cutting tip is proximate a nerve during a surgical cutting procedure.

18. The surgical cutting system of claim 15, wherein the cutting tip is a bur.

19. The surgical cutting system of claim 15, wherein the cutting instrument housing is electrically non-conductive and is provided apart from a housing of the motor assembly such that upon mounting of the cutting instrument to the motor assembly, the cutting instrument housing electrically isolates the electrical pathway from portions of the motor housing otherwise in contact with the cutting instrument housing.

20. The surgical cutting system of claim 15, wherein the housing maintains a conductive spacer of the fluid coupling assembly, which is disposed between the housing and the elongate drive member, and further wherein the electrical connector is coupled to the conductive spacer such that the electrical pathway from the electrical connector to the tip includes the elongate drive member and the conductive spacer.

21. The surgical cutting system of claim 20, wherein the conductive spacer is cylindrically shaped and includes an opening to allow the electrically conductive fluid to flow to the drive member.

22. The surgical cutting system of claim 20, wherein the conductive spacer is porous to allow the electrically conductive fluid to flow to the drive member.

23. The surgical cutting system of claim 20 further comprising:
   an outer tube maintained by the housing, the outer tube defining a proximal region terminating at a proximal end, a distal region terminating at a distal end, and a lumen extending from the proximal end to the distal end;
   wherein the elongate drive member is disposed within the lumen of the outer tube and the conductive spacer is positioned between an inner surface of the outer tube and the elongate drive member.

24. The surgical cutting system of claim 23, wherein the fluid coupling assembly includes tubing adapted for carrying the electrically conductive fluid along an outer surface of the outer tube, the tubing fluidly coupled to the conductive spacer through a port in the outer tube.

25. A method of performing a surgical cutting procedure comprising:
   providing a surgical cutting instrument including:
      an elongate drive member,
      a cutting tip attached to a distal section of the drive member,
      a non-conductive coupling body attached to a proximal section of the drive member,
      a housing maintaining the coupling body and the proximal section of the drive member,
      a fluid coupling assembly in fluid communication with the drive member, the fluid coupling assembly adapted for fluid connection to a source of electrically conductive fluid,
      an electrical connector in electrical communication with the cutting tip via an electrical pathway established by at least the drive member and the fluid coupling assembly;
   electrically connecting an evoked potential monitoring system to the cutting instrument via the electrical connector such that an energy source of the evoked potential monitor system is in electrical communication with the cutting tip;
   mounting the surgical cutting instrument to a motor assembly;
   delivering the cutting tip to a surgical site;
   operating the motor assembly to perform a cutting operation with the cutting tip;
   applying a stimulation energy to the cutting tip via the energy source; and
   detecting a proximity of the cutting tip to a nerve based upon reference to the stimulation energy.

26. The method of claim 25, wherein performing a cutting operation with the cutting tip includes rotating the cutting tip at a speed of at least 20,000 RPM.

27. The method of claim 25, wherein performing a cutting operation and applying a stimulation energy occur substantially simultaneously.

28. The method of claim 25, wherein the method is characterized by the motor assembly continuing to operate while a proximity of the cutting tip to a nerve is detected.

29. The method of claim 25, further comprising:
automatically disabling power delivery to the motor assembly based upon the detected proximity.

30. The method of claim 25, wherein the housing maintains a conductive spacer of the fluid coupling assembly, which is disposed between the housing and the elongate drive member, and further wherein the electrical connector is coupled to the conductive spacer such that the electrical pathway from the electrical connector to the tip includes the elongate drive member and the conductive spacer.

31. The method of claim 30, wherein the conductive spacer is cylindrically shaped and includes an opening to allow the electrically conductive fluid to flow to the drive member.

32. The method of claim 30, wherein the conductive spacer is porous to allow the electrically conductive fluid to flow to the drive member.

33. The method of claim 30 further comprising:
an outer tube maintained by the housing, the outer tube defining a proximal region terminating at a proximal end, a distal region terminating at a distal end, and a lumen extending from the proximal end to the distal end;
wherein the elongate drive member is disposed within the lumen of the outer tube and the conductive spacer is positioned between an inner surface of the outer tube and the elongate drive member.

34. The method of claim 33, wherein the fluid coupling assembly includes tubing adapted for carrying the electrically conductive fluid along an outer surface of the outer tube, the tubing fluidly coupled to the conductive spacer through a port in the outer tube.

* * * * *